United States Patent [19]

Araki et al.

[11] 4,103,997

[45] Aug. 1, 1978

[54] LIGHT SCATTERING TYPE SMOKE DETECTOR

[75] Inventors: Tsunehiko Araki, Takarazuka; Yoshihiko Okuda, Izumi, both of Japan

[73] Assignee: Matsushita Electric Works, Ltd., Osaka, Japan

[21] Appl. No.: 703,201

[22] Filed: Jul. 7, 1976

[30] Foreign Application Priority Data

Jul. 15, 1975 [JP] Japan .................. 50-86793

[51] Int. Cl.$^2$ .................. G01N 21/00; G01N 21/26
[52] U.S. Cl. .................. 356/104; 250/574; 356/103
[58] Field of Search .................. 356/103, 104; 250/574

[56] References Cited

U.S. PATENT DOCUMENTS

| | | | |
|---|---|---|---|
| 3,474,435 | 10/1969 | White | 356/103 |
| 3,505,529 | 4/1970 | Moore | 250/574 |
| 3,524,707 | 8/1970 | Hansen | 356/103 |
| 3,612,689 | 10/1971 | Liskowitz | 356/103 |
| 3,621,220 | 11/1971 | Ford | 356/103 |
| 3,701,620 | 10/1972 | Berkman | 356/103 |
| 3,932,762 | 1/1976 | Moser | 356/103 |

Primary Examiner—Samuel W. Engle
Assistant Examiner—Donald P. Walsh
Attorney, Agent, or Firm—Burns, Doane, Swecker & Mathis

[57] ABSTRACT

A light scattering type smoke detector effectively sensitive both to white and black smokes is provided. A wave length $\lambda$ of an incident light from a light source and a scattered light receiving angle $\theta$ defined by the direction of the incident light and the direction connecting between a smoke particle and a light receiving element are so determined as to satisfy $\lambda \leq 950$ m$\mu$ when $\theta \leq 45°$, $\theta \leq -0.18\lambda + 216$ when $45° \leq 135°$ and $\theta \leq 135°$ when $\lambda \leq 450$ m$\mu$.

5 Claims, 7 Drawing Figures

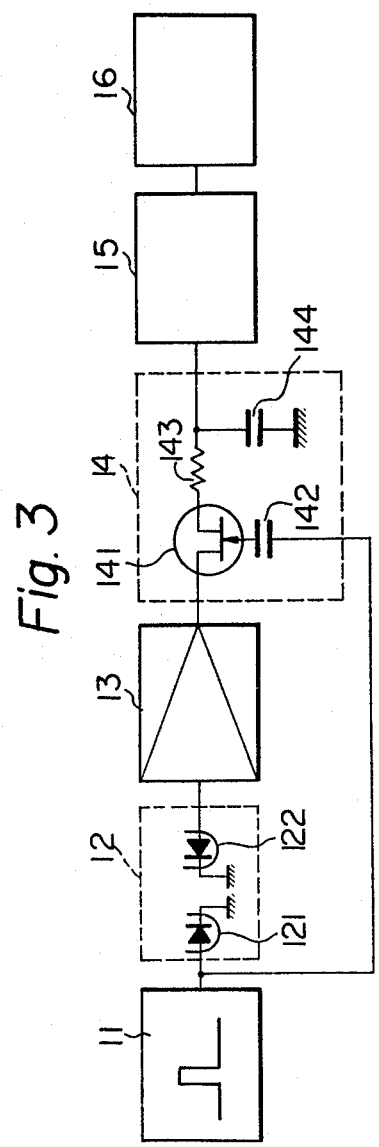
Fig. 3
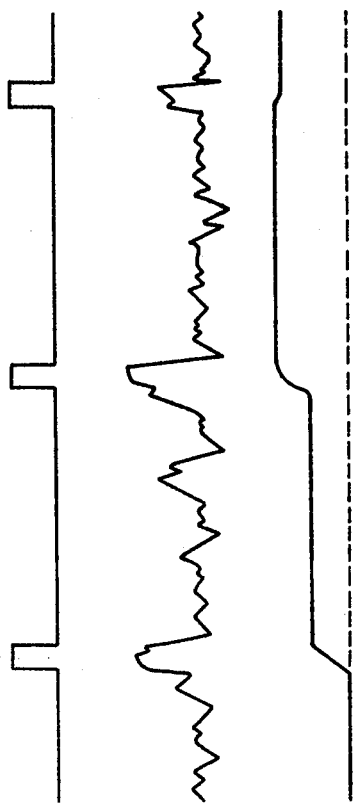
Fig. 4A
Fig. 4B
Fig. 4C

LIGHT SCATTERING TYPE SMOKE DETECTOR

This invention relates to a light scattering type smoke detector wherein a detection of a scattering of emitted light from a light source due to a smoke is utilized for detections of fires.

In conventional light scattering type smoke detectors, mostly a sub-infrared light emitting diode is used for the light source and a scattered light due to a presence of smoke in light beam is received by a photocell disposed at a position in front of the source and in a normal direction with respect to optical axis of the light beam from the source. In this case, generally, the smoke will be a white smoke produced by a smoldering or the like of the cellulose, or a black or dark smoke produced due to a combustion of a petroleum series fuel or the like and the light scattering type smoke detectors are more highly responsive to the white smoke than to the black smoke in such that the detectors are responsive to the white smoke about 10 times as high as they do with respect to the black smoke in the case when, for example, an emitted light with a wave length of 940 m$\mu$ is received as scattered by the photocell at a fore side 135° relation to axis optical axis of the emitted light. On the other hand, it is desirable to set the sensitivity of the detectors to the white smoke properly lower so that, for example, the detectors will be responsive generally to the white smoke showing a light extinction rate of about 10% per meter, whereby the detectors will be prevented from misoperating in response to any dust floating in the atmosphere, the smoke of cigarettes or the like. In this case, however, such detectors will become low sensitive remarkably with respect to the black smoke and they may be unable to act as the detector against fires accompanied mostly by the black smoke. The present invention has been suggested to remove such defect of the known detectors of the kind referred to in such manner that the difference in the sensitivity of the detector to the white smoke and that to the black smoke is made smaller by properly defining the relation between the wave length of incident light and the scattered light receiving angle in the detector and thereby the preventions of misoperations with respect to the white smoke and of any non-response to the black smoke of the detectors will be simultaneously achieved.

According to the present invention, in the light scattering type smoke detector, the above discussed problem has been able to be solved by defining the wave length $\lambda$ of incident light from a light source and the scattered light receiving angle $\theta$ between the direction of the incident light and the direction connecting a smoke particle and a light receiving element such as a photocell so as to satisfy $\lambda \leq 950$ m$\mu$ when $\theta \leq 45°$, $\theta \leq -0.18 \lambda + 216$ when $45° \leq \theta \leq 135°$ and $\theta \leq 135°$ when $\lambda \leq 450$ m$\mu$.

As primary object of the present invention is to provide a smoke detector wherein the fluctuation in the sensitivity is little depending on the kind of smoke.

Another object of the present invention is to provide a smoke detector wherein the sensitivity to the black smoke is high and a non-warning less occurs in the case of fires generating a large amount of black smoke due to kerosene, foamed polystyrol or the like.

A further object of the present invention is to provide a smoke detector wherein the sensitivity is high and the misoperation is little.

Other objects and advantages of the present invention will become clear upon the following explanation of the invention advances detailed with reference to a preferred embodiment of the present invention in conjunction with accompanying drawings, in which:

FIG. 3 is a block circuit diagram of an embodiment of the detector according to the present invention;

FIGS. 4A through 4C show wave forms at respective parts in the circuit of FIG. 3.

Figure 1:
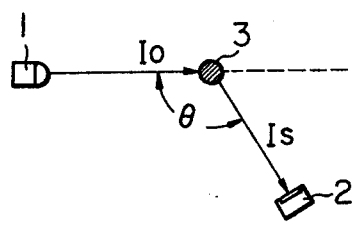
FIG. 1 is an explanatory view of a principle of the light scattering type smoke detector of the present invention.

The present inventors have perceived that, in the arrangement of a light source 1 and a light receiving element 2 such as a photocell as shown in FIG. 1, the intensity ratio $I_s/I_o$ of a scattered light $I_s$ by a smoke particle 3 to an incident light $I_o$ from the light source 1 has a certain relation to the wave length $\lambda$ of the incident light $I_o$ and the scattered light receiving angle $\theta$ (which is an angle between the incident light $I_o$ and scattered light $I_s$), and this has been experimentally confirmed by the inventors. The $I_s/I_o$ ratio for each of a black smoke B (such as, for example, a kerosene burning smoke) and a white smoke W (such as, for example, a cellulose smoldering smoke) is determined by varying the optical wave length $\lambda$ and scattered light receiving angle $\theta$ and the sensitivity ratio B/W of the black smoke to the white smoke is determined as diagrammatically shown in FIG. 2, wherein the wave length $\lambda$ is taken on the abscissa, the scattered light receiving angle $\theta$ is taken on the ordinate and five curves of the sensitivity ratio B/W = 0.1, 0.2, 0.3, 0.4 and 0.5 are shown. It is understood from this diagram that, the shorter the wave length $\lambda$ of the light from the source, the larger the ratio B/W and that, the smaller the scattered light receiving angle $\theta$, the larger the ratio B/W.

Considerations shall be made on the preferable value of the sensitivity ratio B/W. Generally the sensitivity of the smoke detector of the kind referred to can not be said to be the higher the better, because a cigarette smoke or a slight dust floating in air may be apt to cause a miswarning of such detector. Therefore, it is clear in experiences that, if the sensitivity is so set that the light extinction rate (which is a rate of reduction of a light by passing through a smoke) will be about 10% per meter, the reliability will be the highest.

On the other hand, since the smoke detector is related specifically with the beginning of a refuge of persons and a fire extinguishing activity, it must operate with a smoke of a light extinction rate of at least about 30% per meter. This means that the smoke to which the detector should be sensible is of a thickness through which 5 to 10 meters ahead can be seen. Hence, it is preferable that the ratio B/W is 0.3 or more.

Figure 2:
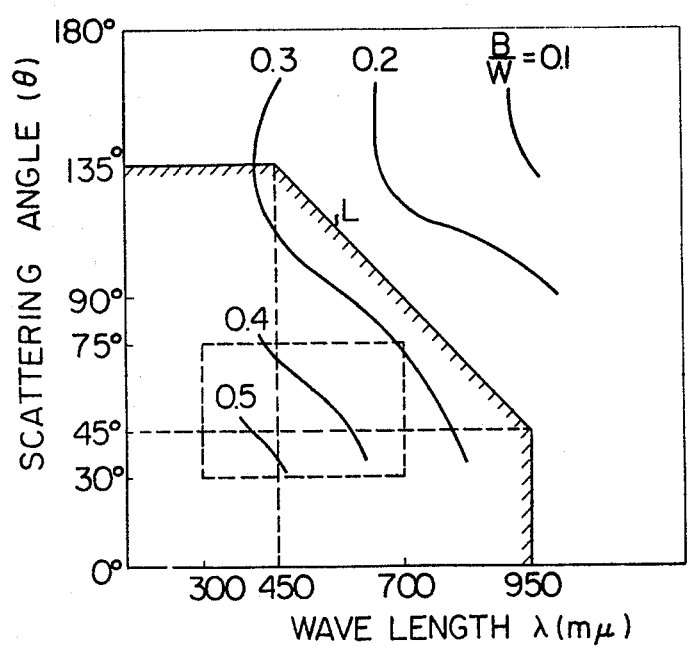
FIG. 2 is a characteristics diagram of the same.

From the above, the range defined as hatched in the diagram of FIG. 2 is preferable, that is:

(i) When $\theta \leq 45°$, $\lambda \leq 950$ m$\mu$.

(ii) When $45° \leq \theta \leq 135°$, $\theta \leq -0.18 \lambda + 216$ (iii) When $\lambda \leq 450$ m$\mu$, $\theta \leq 135°$ The inclined line L in the diagram is represented by $\theta = -0.18 \lambda + 216$. In the actual smoke detector, the scattered light receiving angle $\theta$ of the scattered light received by the light receiving element or photocell has a certain range but the angle $\theta$ referred to here is a scattered light receiving angle contributing to the greater part of the amount of the received light.

For the light source, such light emitting diode as GaAs, GaAsP or GaP or a xenon lamp is used. The light of such source is not monochromatic in the strict sense of the word but has a certain wave length range and the wave length $\lambda$ defined here represents its typical value.

Further, the practically preferable range is of the wave length $\lambda = 300$ to $700$ m$\mu$ and scattered light receiving angle $\theta = 30°$ to $75°$ which are found to be most preferable in view of the design of the smoke detector and the type of light source. In other words, with $\lambda =$ less than $300$ m$\mu$, the light will be impermeable to any glass, and from the viewpoint of the easiness of procurement of the light emitting diodes, $\lambda =$ less than $700$ m$\mu$ is proper. Further, in the design of the smoke detecting chamber, the angle $\theta = 30°$ is a limit and, from the intersection of the curve of B/W $= 0.3$ and $\lambda = 700$ m$\mu$, $\theta = 75°$ is determined.

The structure of the smoke detector most preferable to work the present invention shall be described in the following.

The embodiment shall be referred to with reference to the case where a light emitting GaAsP diode emitting a light of a wave length $\lambda = 640$ is used and a scattered light receiving angle $\theta = 60°$. In this respect, the case of $\theta = 30°$ to $75°$ is the same.

With this angle, the ratio $I_s/I_o$ of the scattered light is so small in the experiment that it is difficult to obtain a signal sufficient for a noise generated from a light receiving silicon photo diode itself and/or an amplifier connected with it or, for example, a heat noise generated from a resistor as well as for a foreign noise leaking through a light labyrinth of the smoke detector.

This problem can be reduced by a known method wherein a light emitting diode is driven with a pulse current source of a very small duty so as to momentarily obtain a large light output as taught, for example, in Swiss Patent No. 417,405. That is, with the momentary feed of such electric power as will immediately bring about a destruction by an ordinary direct current feed, an amount of emitted light 10 to 20 times as large will be obtained and, as a result, the signal per noise ratio can be elevated. In a detector emitting such pulsating light, in some case, there is carried out a method wherein a signal will be interrupted in an amplifying circuit in a light emission stopping period so as to reduce the possibility of a misoperation being made by a foreign noise. However, in such method, there is no effect on a constant noise generated from the light receiving element itself and/or amplifying circuit.

In the embodiment of the present invention, a CR integrating circuit having a time constant several times as large as that of a light emitting period is loaded through a switch in an amplifying circuit for definitely detecting a scattered light signal from various noises. This switch is closed as synchronized with the light emitting period. By integrating the signal in this light emitting period over several periods, noises represented by the same positive and negative probabilities are to be canceled.

In FIG. 3 showing a practical circuit arrangement, 11 is a pulse current source for driving a light emitting diode 121 in a detecting chamber 12, the pulse width is about 100 m$\mu$, the period is about 1 second and 1 ampere is fed to the light emitting diode 121. An output of about 100 PA is obtained from a light receiving photocell 122, which is amplified by an amplifying circuit 13 and is given to a signal processing circuit 14 which is formed of a field effect transistor 141 and an integrating circuit of a resistance 143 and condenser 144. The pulses from the pulse current source 11 are given through a condenser 142 to the gate of the field effect transistor 141 so that, whenever each pulse arrives, a switch (between the source and the drain of the field effect transistor) will be ON. Therefore, during the light emitting period, the field effect transistor 141 will become a low resistance and a signal voltage including a noise will be accumulated in the condenser 144 through the resistance 143. This light emitting period is about a fraction of the time constant of CR and is so small that the voltage of the condenser will be elevated but slightly by the output from the light receiving element and, during the non-light emitting period, there will be a high resistance between the source and the drain of the field effect transistor 141 and the voltage of the condenser 144 will not be elevated by a noise. During the next light emitting period, the voltage of the condenser 144 will be again elevated by the output from the light receiving element, thus the condenser voltage will gradually become higher and, when it reaches a certain value, it will operate a threshold value circuit 15 so that a warning device 16 or the like will be thereby operated.

In FIG. 4 showing voltage wave forms, FIG. 4A is of the pulse voltage, FIG. 4B is of the output voltage from the amplifier 13 when a smoke is present and FIG. 4C is of a terminal voltage of the condenser 144. According to the present invention, as an integrating circuit is provided, positive and negative noises will be added together and averaged to be zero so that their influence will remarkably reduced.

Figure 5:
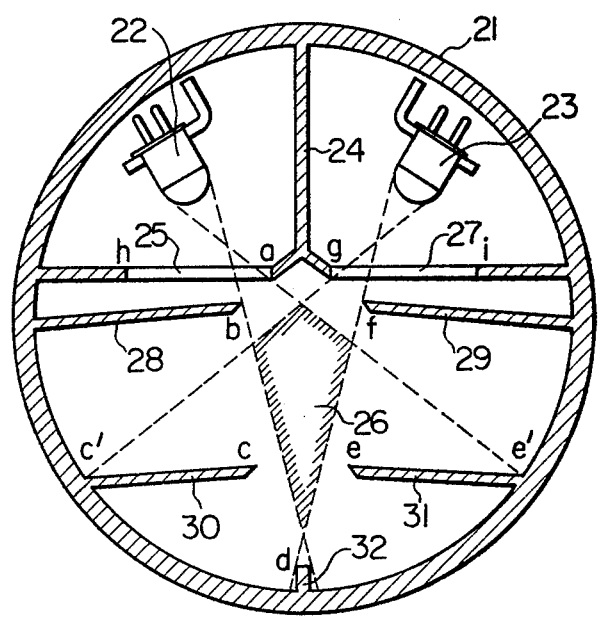
FIG. 5 shows an exemplary structure of a smoke detecting chamber in the smoke detector.

Referring next to FIG. 5 showing an example of the structure of smoke detecting chamber, a light source 22 and a photocell 23 are disposed as separated by a separator 24 within a cylindrical housing 21 so that a light projected onto smoke particles present in a region 26 shown as hatched through a window 25 will become a scattered light which reaches the photocell 23 through a window 27. In the arrangement, light intercepting plates 28 to 32 are provided within the housing 21 so that the relations of the respective tip edges "a" through "i" and base positions c' and e' of the windows and light intercepting plates will be as follows. The smoke is to come in and out in the axial directions of the cylindrical housing, the edge "a" of the window 25 is so determined that the light from the light source 22 will not reach the edges "g" and "f," the edge "b" of the light intercepting plate 28 is so determined that the light will not directly reach a fore field of vision of the photocell 23 between the base c' of the wall 30 and the edge "d" of the plate 32, the edges "g" and "f" are so determined as to limit the field of vision of the photocell and the edges "c," "d," "e," "h" and "i" are to prevent the second reflection within the housing, that is, to prevent the surfaces in the field of vision of the photocell from being within the surfaces to which the light is irradiated directly from the light source 22.

According to the present invention, as described above, even the black smoke can be positively detected by the detector because of the specified relations of the wave length of an incident light and the scattered light receiving angle.

Further, with the provision of the integrating circuit as a detecting circuit, an effect of preventing any misoperation of the detector from occurring due to any noise can be brought about.

What is claimed is:

1. In a smoke detector of the light scattering type for actuating a warning device and comprising a housing containing a light source for emitting incident light having a wave length $\lambda$, a light receiving element, and a smoke collecting region so arranged that incident light from said source which contacts a smoke particle in said region is scattered such that the scattered light directed toward said receiving element forms an angle $\theta$ with the direction of the incident light, the ratio of the intensity $I_s$ of the scattered light to the intensity $I_o$ of the incident light defining an intensity ratio $I_s/I_o$ for the smoke; the ratio of the intensity ratio for a black smoke to the intensity ratio for a white smoke defining the sensitivity ratio of the detector; the improvement wherein said wave length $\lambda$ and said angle $\theta$ each bear a relationship to the intensity ratio and are determined as a function of one another within the limits $\lambda \leq 950$ m$\mu$ when $\theta \leq 45°$, $\theta \leq -0.18\lambda + 216$ when $45° \leq \theta \leq 135°$, and $\theta \leq 135°$ when $\lambda = 450$ m$\mu$, to define a preselected range of sensitivity ratios for the detector.

2. A detector according to claim 1 wherein said wave length $\lambda$ is 300 to 700 m$\mu$ and said scattered light receiving angle $\theta$ is 30 to 75°.

3. A detector according to claim 2 wherein said light source is driven by a voltage of a pulse wave form.

4. A detector according to claim 3 wherein an output from said light receiving element is applied to an integrating circuit through a switch element conducted only while said light emitting element is excited by said pulse wave voltage and, when an integrated value in said integrating circuit reaches a threshold value, a warning signal is provided.

5. A detector according to claim 1 wherein the sensitivity ratio is 0.3 or more.

* * * * *